United States Patent
Li et al.

(10) Patent No.: US 10,576,266 B2
(45) Date of Patent: *Mar. 3, 2020

(54) TITANIUM ALLOY CONTACT RING ELEMENT HAVING LOW MODULUS AND LARGE ELASTIC ELONGATION

(71) Applicant: MEDTRONIC, INC., Minneapolis, MN (US)

(72) Inventors: Bernard Q. Li, Plymouth, MN (US); Alan Shi, Plymouth, MN (US); Daniel D. Sorensen, Blaine, MN (US); Darren A. Janzig, Center City, MN (US); Margaret Bush, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 163 days.

This patent is subject to a terminal disclaimer.

(21) Appl. No.: 15/609,142

(22) Filed: May 31, 2017

(65) Prior Publication Data
US 2017/0259055 A1    Sep. 14, 2017

Related U.S. Application Data

(63) Continuation of application No. 14/640,469, filed on Mar. 6, 2015, now Pat. No. 9,694,173.
(Continued)

(51) Int. Cl.
*C22C 14/00* (2006.01)
*C22F 1/18* (2006.01)
(Continued)

(52) U.S. Cl.
CPC .............. *A61N 1/05* (2013.01); *A61N 1/00* (2013.01); *A61N 1/3752* (2013.01); *B23H 9/00* (2013.01);
(Continued)

(58) Field of Classification Search
CPC ....... A61N 1/3752; C22F 1/183; C22C 14/00; B23H 9/00
See application file for complete search history.

(56) References Cited

U.S. PATENT DOCUMENTS 7,711,428 B2    5/2010    Janzig et al.
9,409,008 B2 *  8/2016    Li .......................... A61N 1/05
(Continued)

FOREIGN PATENT DOCUMENTS

WO    WO 2015/134859 A1    9/2015

OTHER PUBLICATIONS

WO 2015/134859 A1 (PCT Patent Application No. PCT/US2015/019154); International Search Report / Written Opinion dated Jun. 15, 2015, 11 pages.
(Continued)

*Primary Examiner* — William J Levicky
(74) *Attorney, Agent, or Firm* — Mueting, Raasch, and Gebhardt, P.A.

(57) ABSTRACT

A method of forming a medical device contact element includes annealing an elongated rod of Ti-15Mo alloy material to form an annealed rod having a Young's Modulus of less than 13.5 Mpsi and an elastic range or strain of at least 0.7%. Then forming a contact ring element from the annealed rod and assembling the contact ring element into a medical device. Contact rings and lead receptacles including the same are also described.

19 Claims, 5 Drawing Sheets

Related U.S. Application Data

(60) Provisional application No. 61/949,343, filed on Mar. 7, 2014.

(51) Int. Cl.
    *A61N 1/375*     (2006.01)
    *B23H 9/00*     (2006.01)
    *A61N 1/05*     (2006.01)
    *A61N 1/00*     (2006.01)

(52) U.S. Cl.
CPC .............. *C22C 14/00* (2013.01); *C22F 1/183* (2013.01); *Y10T 29/49826* (2015.01); *Y10T 29/49872* (2015.01)

(56) References Cited

U.S. PATENT DOCUMENTS

| | | | |
|---|---|---|---|
| 2005/0084672 A1 | 4/2005 | O'Brien | |
| 2006/0231178 A1 | 10/2006 | Lin et al. | |
| 2010/0063555 A1* | 3/2010 | Janzig | A61N 1/3752 607/2 |
| 2012/0060981 A1* | 3/2012 | Forbes Jones | C22C 14/00 148/649 |
| 2012/0271381 A1 | 10/2012 | McIntyre et al. | |
| 2012/0271385 A1 | 10/2012 | Li et al. | |
| 2012/0271386 A1* | 10/2012 | Li | C22C 14/00 607/116 |

OTHER PUBLICATIONS

ATI Allvac Technical Data Sheet, "ATI Ti—15Mo Beta Titanium Alloy," Mar. 21, 2008. Retrieved from the Internet on Oct. 26, 2015, at <http://sei.ckcest.cn/product_img/100001/8477/538474/Document/Ti-075%20Ti-15Mo.pdf>, 3 pages.

Davis et al., "Martensitic transformation in Ti—Mo alloys", Mar. 1979, *Journal of Materials Science*, 14(3):712-722.

Disegi, "Implant Materials. Wrought Titanium-15%Molybdenum, Second Edition", Apr. 2009, Synthes, Inc. (USA), West Chester, Pennsylvania. 32 pages.

Donachie Jr., "Heat Treating Titanium and Its Alloys," *Heat Treating Progress*, Jun./Jul. 2001; 47-57.

Ho et al., "Structure and properties of cast binary Ti—Mo alloys", Nov. 1999, *Biomaterials*; 20(22):2115-2122.

Murray, "Mo—Ti (Molybdenum-Titanium)" phase diagram screen print from *ASM Handbook vol. 3: Alloy Phase Diagrams*. Baker (Ed.), ASM International, Materials Park, Ohio, 1992.

Nag et al., "Comparison of microstructural evolution in Ti—Mo—Zr—Fe and Ti—15Mo biocompatible alloys", Jul. 2005, *Journal of Materials Science: Materials in Medicine*; 16(7):679-685.

Zardiackas et al., "Characterization of Ti—15Mo Beta Titanium Alloy for Orthopedic Implant Applications", *Medical Applications of Titanium and Its Alloys: The Material and Biological Issues*, ASTM STP 1272. Brown et al. (Ed.), ASTM West Conshohocken, Pennsylvania, May 1996. Cover/title page, Cataloging and copyright page, and pp. 60-87.

European Patent Application No. 15717061.4, filed Mar. 6, 2015; European Examination Report dated Apr. 5, 2018.

\* cited by examiner

TITANIUM ALLOY CONTACT RING ELEMENT HAVING LOW MODULUS AND LARGE ELASTIC ELONGATION

CROSS-REFERENCE TO RELATED APPLICATIONS

The present application is a continuation application of U.S. patent application Ser. No. 14/640,469, filed March 6, 2015, which claims priority to U.S. Provisional Patent Application Ser. No. 61/949,343, filed Mar. 7, 2014, the disclosures of which are incorporated herein by reference in their entirety.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes disposed on a distal end portion of a lead. The proximal end portion of a lead typically contains a number of connector rings corresponding to the number of electrodes. Conductors run within and along the lead body and electrically couple the connectors to the electrodes. The proximal end portion of the lead is inserted into lead receptacle of a signal generator such that electrical contact is made between discrete contacts in the receptacle and the connector rings of the lead.

The contacts of the receptacle typically include a garter spring within a ferrule. The ferrule is typically electrically coupled to a feedthrough that provides electrical coupling with electronics of the device. The garter spring contacts a contact ring of a lead, electrically coupling the lead to the device electronics via the ferrule and feedthrough. While such lead receptacle contacts have been proven to perform very well over time, garter rings are difficult to manufacture and must provide two contacts for proper electrical connection: one contact with the lead connector ring, and the other with the ferrule. Further, because of the spring configuration, the spring contacts the lead connector ring and the ferrule at multiple points, with each separate contact resulting in increased electrical resistance. Such resistance could result in undesirably large power consumption. Improvements with these contact elements are desired.

SUMMARY

The present disclosure relates to a contact element formed of a titanium alloy that has a low modulus and large elastic elongation or large elastic recovery. This titanium alloy provides a reduced insertion force and extended elastic range when utilized in a medical device lead connector contact ring element. Methods of forming the contact ring element are also disclosed.

In one illustrative embodiment, a method of forming a medical device contact element includes annealing an elongated rod of Ti-15Mo alloy material to form an annealed rod having a Young's Modulus of less than 13.5 Mpsi and an elastic range of at least 0.7%. Then forming a contact ring element from the annealed rod and assembling the contact ring element into a medical device.

In another illustrative embodiment, a contact ring element for electrically coupling a medical lead to an implantable medical device, includes a tubular body defining a cavity configured to receive a lead and a plurality of resiliently deflectable elements extending from the tubular body in to the cavity, and each of the resiliently deflectable elements having a lead contacting portion configured to contact a lead then the lead is received in the cavity. The resiliently deflectable elements are formed of a Ti-15Mo alloy material having a Young's Modulus of less than 13.5 Mpsi and an elastic range of at least 0.7%.

In a further illustrative embodiment, a lead connector or lead receptacle for electrically coupling a medical lead to an implantable medical device includes a contact ring element as described herein and an insulating ring axially aligned with the contact ring element.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
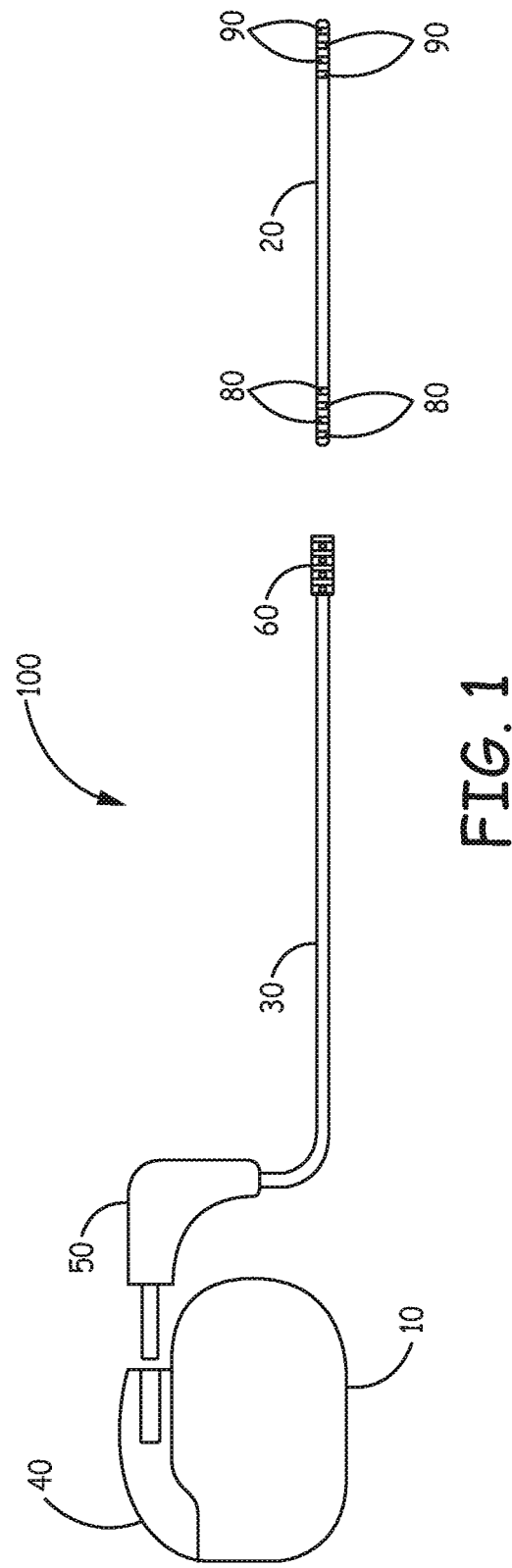
FIG. 1 is a schematic diagram of an exploded view of a representative implantable active electrical device and associated lead and extension.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

As used herein, "active implantable electrical device" or the like refers to a device that is capable of generating, sending or receiving an electrical signal via a medical lead.

As used herein, "tubular" means having the shape and configuration of a tube. "Tube", as used herein means a hollow object having a body and a cavity extending through the body. A tube may take any suitable shape, such as a cylinder, a cuboid, or the like.

The present disclosure relates to a contact element formed of a titanium alloy that has a low modulus and large elastic elongation. The titanium alloy can be a beta-titanium alloy such as a Ti-15Mo alloy for example. This titanium alloy provides a reduced insertion force and extended elastic range when utilized in a medical device lead connector or lead receptacle contact ring element. Methods of forming the contact ring element are also disclosed. The contact ring element can be a tubular element that includes a plurality of resiliently deflectable elements that are formed of the titanium alloy material having a Young's Modulus of less than 13.5 Mpsi or less than 13 Mpsi or less than 12.5 Mpsi or less than 12 Mpsi while having an elastic range of at least 0.7% or at least 0.8% or at least 0.9% or at least 1% or at least 1.1% or at least 1.2% or an elastic range upper value in a range from 1 to 2%. These physical properties of the resiliently deflectable elements provides for unique features when utilized in a lead receptacle for a medical device. For example, a lead receptacle having these contact elements has a reduced lead insertion force into the lead receptacle thus, a lead can be easily inserted the lead receptacle. At the same time the resiliently deflectable elements securely contact the lead body and elastically move relative to inserting and removing the lead from the lead receptacle. In other words, the resiliently deflectable elements do not plastically or permanently deform upon insertion of the lead into the lead receptacle. In many embodiments these contact ring elements are monolithic or "one-piece" elements. While the present disclosure is not so limited, an appreciation of various aspects of the disclosure will be gained through a discussion of the examples provided below.

Figure 2:
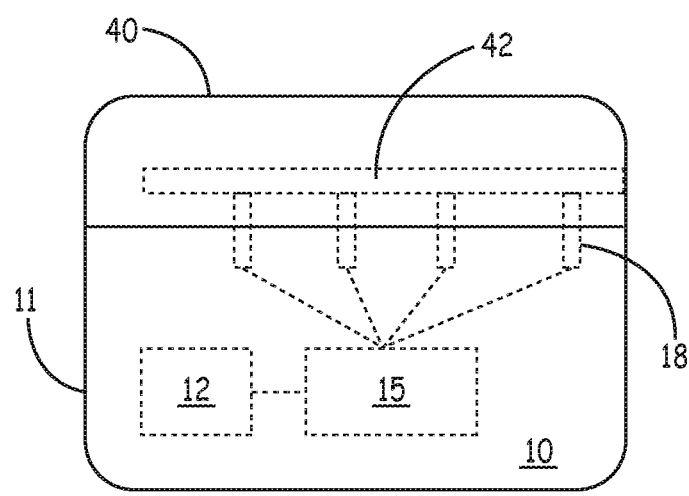
FIG. 2 is a schematic diagram of a side view of an active implantable medical device with representative internal components shown in dashed lines.
Figure 3:
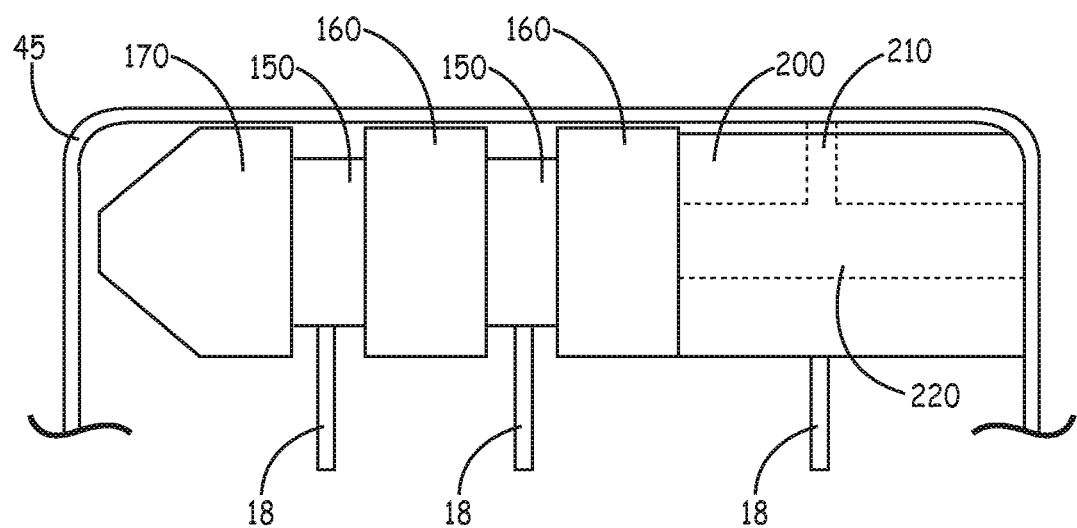
FIG. 3 is a schematic cut away side view of an illustrative lead connector or lead receptacle of the device depicted in FIG. 2 with representative internal components shown in dashed lines.

FIG. 1 is a schematic diagram of an exploded view of a representative implantable active electrical device and associated lead and extension. FIG. 2 is a schematic diagram of a side view of an active implantable medical device with representative internal components shown in dashed lines. FIG. 3 is a schematic cut away side view of an illustrative lead receptacle of the device depicted in FIG. 2 with representative internal components shown in dashed lines.

Referring to FIG. 1, a schematic of an exploded view of a representative implantable medical device system 100 in which the annealed Ti alloy material contact ring element may be employed is shown. The system 100 includes an implantable active electrical device 10, and a lead 20 operably couplable to active electrical device 10. Active electrical device 10 may be any electrical signal generator or receiver useful for delivering therapy to a patient or for patient diagnostics. For example, active electrical device 10 may be a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. As shown in FIG. 1, the system 100 may include a lead extension 30 or other adaptor to couple lead 20 to active electrical device 10. While not shown, it will be understood that more than one lead 20 may be operably coupled to one active electrical device 10 or one extension 30 or that more than one extension 30 may be operably coupled to one active electrical device 10. It will also be understood that lead 20 may be coupled to active electrical device 10 without extension 30 or adaptor.

Active electrical device 10 may include a connector header 40 for connecting to lead 20 or extension 30 or other adaptor to couple lead 20 to active electrical device 10. In the embodiment depicted in FIG. 1, the connector header 40 is configured to receive a proximal connector portion 50 of a lead extension 30. The extension 30 includes a distal connector 60 configured to receive proximal end of lead 20. Distal connector 60 has internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown) within the body of the lead 20. Lead 20 may include any number of electrodes 90, e.g. one, two, three, four, five, six, seven, eight, sixteen, thirty-two, or sixty-four. Typically, each electrode 90 is electrically coupled to a discrete electrical contact 80. For the purposes of the remainder of this disclosure, "lead" and "lead extension" are used interchangeably.

Referring now to FIG. 2, a schematic side view of a representative active implantable electrical device 10 is shown, with selected internal components shown in dashed lines. The device 10 includes a header 40 having a lead receptacle or lead receptacle 42 extending therein. The lead receptacle 42 is configured to receive a proximal portion of a lead, extension or adaptor. The receptacle 42 includes one or more electrically conductive portions or contact ring elements (not shown) configured to electrically couple with proximal contacts 80 of a lead 20 or lead extension. The conductive portions are electrically coupled to electronics 15 disposed within hermetically sealed device housing 11. Hermetically sealed electrical feedthroughs 18 may be used to couple conductive portions of the receptacle 42 to the electronics 15. In the depicted embodiment, the electronics 15 are operably coupled to a power source 12, such as a battery, capacitor, or the like. The header 40 may be attached to hermetically sealed housing 11 of device 10 by, for example, fasteners, adhesives, welds, or the like.

In some embodiments (not shown), the lead receptacle 42 extends within a hermetically sealed housing 11. In such embodiments, device 10 may not include a header 40 and feedthroughs 18. Any suitable hermetically sealed receptacle may be employed in such embodiments, such as those described in U.S. Pat. No. 7,711,428 B1, entitled "Hermetic Lead Connector Assembly", which is hereby incorporated herein by reference in its entirety to the extent that it does not conflict with the disclosure presented herein.

In FIG. 3, schematics of a cut away side view of an embodiment of a header 40 of FIG. 2 are shown. In the depicted embodiment, exterior portions of the lead receptacle are shown. In FIG. 3, dashed lines represent bores 210, 220 formed in set screw block 200. The receptacle includes alternating conductive 150 and insulating 160 ring sections. The conductive sections 150 are positioned such that when a lead is inserted into the receptacle, a contact on proximal portion may be electrically coupled with a conductive section 150. The conductive sections 150 of the receptacle are electrically coupled to feedthroughs 18 that couple the conductive sections 150 to electronics of the device. Set screw block 200 of the receptacle may be fixed relative to housing 45. The lead receptacle may include an end cap 170. End cap 170 may fit snuggly against housing 45 or other feature such that an axially compressive force is applied to the receptacle. Set screw block 200 defines a lead receiving bore 220 and a second bore 210 configured to receive a set screw. The second bore 210 is generally perpendicular to and intersects with the lead receiving bore 220. In the depicted embodiment, set screw block 200 is conductive and is electrically coupled to a feedthrough 18 that serves to electrically couple the block 200 to electronics of the device.

While the lead receptacle depicted in FIG. 3, include a set screw block, it will be understood that any mechanism for retaining a lead other than a set screw may be employed. It will also be understood that the lead receptacles described herein are applicable to devices having headers that are not fully enclosed by a housing. Such headers are well known and are typically open-faced. Lead receptacles are typically sealed to such header housings with medical adhesive and are back-filled with medical polymeric material, such as silicone, to provide a seal between the electrically conductive portions of the lead receptacle and tissue or fluid of a patient when implanted.

Figure 4:
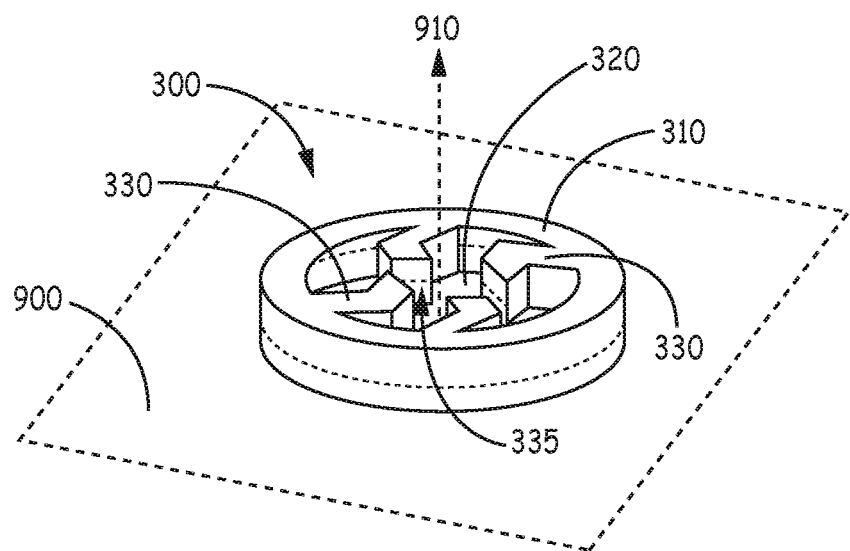
FIG. 4 is a schematic diagram of a perspective view of an illustrative embodiment of an electrical contact ring.
Figure 5:
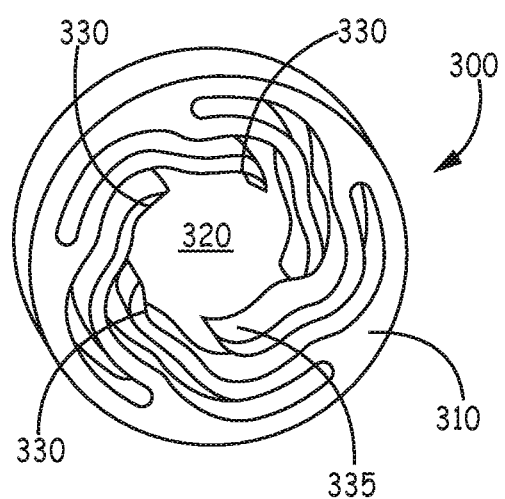
FIG. 5 is a schematic diagram of a perspective view of another illustrative embodiment of an electrical contact ring.

FIG. 4 is a schematic diagram of a perspective view of an illustrative embodiment of an electrical contact ring 300. FIG. 5 is a schematic diagram of a perspective view of another illustrative embodiment of an electrical contact ring 300.

Referring now to FIGS. 4-5, representative embodiments of one-piece electrical connector contact rings or contact ring elements 300 that may serve as conductive portions 150 of a lead receptacle are shown. The depicted contact rings 300 include a tubular body 310 defining a cavity 320 extending through the body 310. The cavity 320 is configured to receive a lead. The contact ring 300 includes a plurality resiliently deflectable elements 330. The deflectable elements 330 have lead contacting portions 335 configured to contact a contact of a lead when the lead is inserted into the cavity 320. The lead contacting portions 335 of the deflectable elements 330, in a relaxed state, are located in a plane 900 that intersects the tubular body 310. The lead contacting portions 335 are configured to deflect along the plane 900 towards the tubular body 320 as the lead is inserted in the cavity 320. As shown in FIG. 4, the plane 900 may be orthogonal to the central axis 910 of the cavity 320. The dashed lines on the tubular body 310 and contacting portions 335 of the deflectable elements 330 shown in FIG. 4 depict the location of intersection of the plane 900.

In FIG. 5, the deflectable members 330 extend into the cavity 320 in a non-radial manner (in a direction not along a radius). As a lead is inserted into the cavity 320 of contact 300, elements 330 deflect outwardly (relative to axial center of contact 300) in a non-radial manner in the depicted embodiment. While portions of the elements 330, such as lead contacting portion 335, may deflect outwardly in a radial manner, the overall element 310 is configured to deflect non-radially when a lead is inserted. That is, the sum total of vectors of deflection along the length of an element 330 is non-radial. As used herein, "non-radial" with regard to outward deflection means deflection in a direction other than along a line defined by a radius.

As shown in FIG. 5, the lead contacting portions 335 of deflectable elements 300, in a relaxed state, are located along a circumference of an imaginary circle concentric with the tubular body 310. The imaginary circle has a diameter that is smaller than the outer diameter of the portion of the lead that the lead contact portions 335 are configured to contact. As the lead is inserted, the elements 330 deflect outwardly (relative to axial center of contact ring 300) to accommodate insertion of the lead. The resilient nature of the deflectable elements 330 biases the contacting portions 335 toward the circumference of the imaginary circle, forcing the contacting portions 335 against the inserted lead. Of course, if the contact of the lead, with which the lead contacting portions 335 are configured to contact, have an exterior shape different from a cylinder (e,g, cuboid), the lead contacting portions 335 may be configured to located along an imaginary shape (e.g., rectangle) similar in shape to the contact of the lead.

The deflecting elements 330 shown in FIGS. 4 and 5 are arcuate or substantially arcuate. The deflected elements may be generally linear. However, it will be understood that deflecting elements 330 may be of any suitable shape. Useful contact ring elements are described in U.S. 2010/0063555, entitled "ELECTRICAL CONTACT FOR IMPLANTABLE MEDICAL DEVICE", which is hereby incorporated herein by reference in its entirety to the extent that it does not conflict with the disclosure presented herein.

In various embodiments, the contact rings are monolithic (formed from a single material without joints or seams). Such monolithic contact rings (which can be of any suitable size, e.g. as described above) may improve the electrical properties of the contact ring relative to other contact rings, which employ a variety of materials or which require welding or other coupling between parts. By employing the same seamless material throughout, electrical resistance due to flow of electrons between the junctions of differing materials can be reduced, which can advantageously reduce the power requirement of devices employing the contact rings.

Contact rings 300 as described herein may be of any suitable size for use in implantable medical devices. For example, the contact rings 300 may have a thickness (axial length) between about 0.10 inches (2.5 millimeters) and about 0.01 inches (0.25 millimeters). In some embodiments, the contact rings 300 have a thickness of between about 0.75 inches (2 millimeters) and about 0.025 inches (0.6 millimeters); e.g., about 0.05 inches (1.2 millimeters). In numerous embodiments, contact rings 300 have a thickness that is approximately the same as the thickness of a ring contact of a lead to which the contact ring 300 is to be electrically coupled. The contact rings 300 may be of any suitable inner and outer diameter. For example, the contact rings 300 may have an outer diameter of between about 0.200 inches (5 millimeters) and 0.05 inches (1.2 millimeters). In some embodiments, the contact rings 300 have an outer diameter of about 0.1 inches (2.5 millimeters) or about 0.11 inches (2.8 millimeters). Generally, the inner diameter of the contact rings 300 (or the diameter formed by lead contacting portions 335 of the deflectable elements 330) is suitable for insertion of a lead.

The deflectable elements 330 of the contact rings 300 may have any suitable length and thickness, which may vary depending on the material from which they are formed. The length will vary depending on the outer diameter of the ring and desired inner diameter formed from lead contacting portions 335 of the deflectable elements 330. In various embodiments, the deflectable elements 330 may have a thickness of between about 0.01 inches (0.25 millimeters) and about 0.001 inches (0.025 millimeters). In some embodiments, the deflectable elements 330 may have a thickness of between about 0.006 inches (0.15millimeters) and about 0.002 inches (0.05 millimeters). The thickness of the deflectable elements 330 may be substantially the same along the length of the element or may vary along the length of the element. In some embodiments, the element 330 is thicker at the base and thinner at the lead contacting portion 335.

It will be understood that a contact ring 300 may include any suitable number of deflectable elements 330. For example, a contact ring may have between 1 and 100 or more deflectable elements. In some embodiments, the contact ring has between 3 and 6 or between 4 and 5 deflectable elements. All other thing being equal, the smaller the number of deflectable elements, the less force required to insert a lead through the cavity of the contact ring. However, if the insertion force is too low, the quality of electrical contact between the lead and the contacting portions of the deflectable elements may be poor. That is, greater resilient force pressing against the lead may lead to better quality and more reliable electrical contact, but may also result in greater insertion force. The number of deflectable elements included in a ring contact may be varied to achieve a desirable balance between quality and reliability of electrical contact and insertion force. In addition, it may be desirable to decrease the number of contact points between the lead and the contact ring, as each point of contact may incrementally increase electrical resistance. Thus, in some embodiments, the lowest number of deflectable element that can provide high quality and reliable electrical contact with the lead is employed.

Contact rings 300 as described herein may be formed by any suitable process. For example, various components may be machined, or otherwise formed. In various embodiments, contact rings are formed by removing a solid portion of a cylinder to form the ring contact. These cylinders can be formed by dividing them from an elongated rod of material such as the annealed titanium alloy described below.

Any suitable method may be used to remove appropriate portion(s) of the cylinder. For example, electrical discharge machining, laser cutting, water jet cutting, photo-etching, or the like may be used to remove appropriate portion(s) of the cylinder. One example of electrical discharge machining that may be employed is wire electrical discharge machining; e.g., with a 0.004 inch wire.

Figure 6:
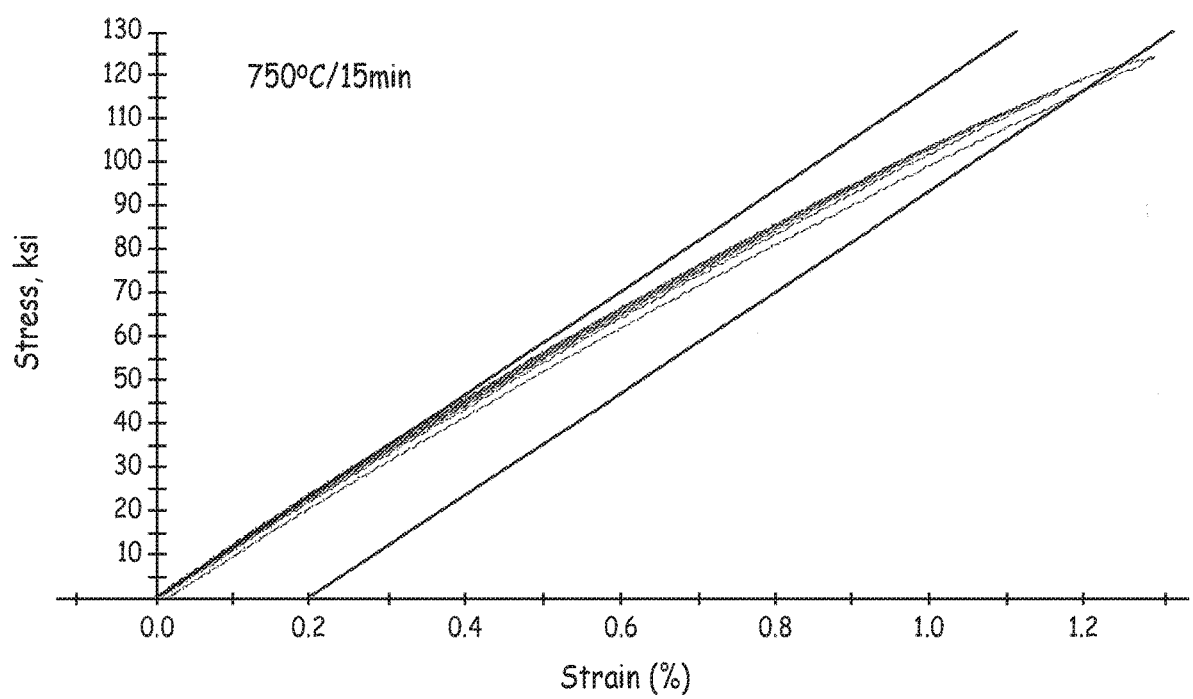
FIG. 6 is a graph of Stress versus Strain (or elastic range) of an Ti-15Mo alloy annealed at 750 degrees centigrade for 15 min and then water quenched.
Figure 7:
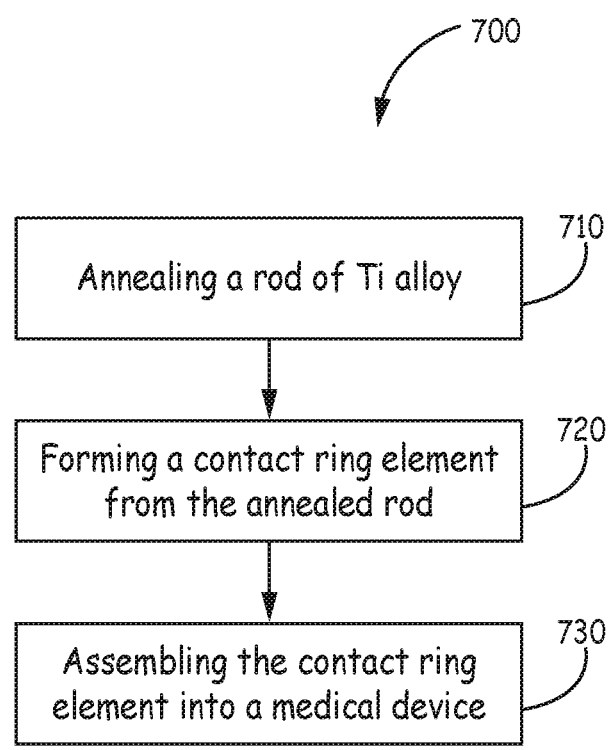
FIG. 7 is a flow diagram of an illustrative method of forming a medical device contact element.

FIG. 6 is a graph of Stress versus Strain (or elastic range) of an Ti-15Mo alloy annealed at 750 degrees centigrade for 15 min and then water quenched. FIG. 7 is a flow diagram of an illustrative method 700 of forming a medical device contact element 300.

Applicants have discovered that annealing a specific titanium alloy to a specific temperature range and time interval and then quickly cooling or quenching provides a material that has a low modulus and large elastic elongation as illustrated in FIG. 6. This material is particular useful as resiliently deflectable elements of the contact ring described herein.

A method of forming a medical device contact element includes annealing an elongated rod of Ti-15Mo alloy material to form an annealed rod having a Young's Modulus of less than 13.5 Mpsi and an elastic range of at least 0.7%. Then forming a contact ring element from the annealed rod and assembling the contact ring element into a medical device.

The term "Ti-15Mo" refers to a metastable beta-titanium alloy that includes about 15 weight percent molybdenum. Ti-15Mo material usually has a Young's Modulus of 15 Mpsi or greater and an elastic range of 0.6% or less and a tensile yield strength of about 120 kpsi. The physical properties described herein are determined using ASTM methods.

Cylinders of Ti-15Mo material can be formed by dicing up an elongated rod of Ti-15Mo material to the appropriate thickness as described above. The elongated rod and corresponding cylinders of material can have any useful diameter as described above, such as 2 mm or greater or 3 mm or greater or 4 mm or greater or less than 10 mm or less than 7 mm or less than 5 mm. The contact ring elements having a tubular body defining a cavity and a plurality of resiliently deflectable elements extending into the cavity can then be formed as described above. Lead connectors or lead receptacles can be formed by axially aligning one or more of the contact ring elements with one or more electrically insulating ring elements and disposing the lead connectors or lead receptacles into a medical device.

FIG. 6 is a graph of Stress versus Strain (or elastic range) of an Ti-15Mo alloy annealed at 750 degrees centigrade for 15 min and then water quenched. However similar physical properties have been produced in Ti-15Mo material by annealing at a temperature in a range from 725 degrees centigrade to 775 degrees centigrade for a time from 5 to 30 minutes or from 5 to 20 minutes for a rod with cold work between 45% to 90% prior annealing. One particularly useful annealing process includes annealing the Ti-15Mo rod in a range from 740 to 750 degrees centigrade for 10 to 20 minutes or about 15 minutes immediately followed by a water quench to quickly cool the annealed rod and prevent the formation of a metastable omega ($\omega$) phase. Cooling the rod from the annealing temperature to room temperature (about 24 degrees centigrade) in less than 24 seconds or less than 20 seconds aids in reducing or preventing the formation of a metastable phase.

One important factor is the quick quench of the heated Ti-15Mo material, as described above. For example the heated Ti-15Mo material can be water quenched and prevent the formation of alpha and/or omega metastable phase material in the Ti-15Mo material. For example the annealed Ti-15Mo material has less than 3 weight percent alpha-phase titanium, or less than 2.5 weight percent alpha-phase titanium, or less than 2 weight percent alpha-phase titanium, or in a range from 0.1 to 3 weight percent alpha-phase titanium, or in a range from 0.1 to 2 weight percent alpha-phase titanium.

The annealed Ti-15Mo material has a Young's Modulus of less than 13.5 Mpsi or less than 13 Mpsi or less than 12.5 Mpsi or less than 12 Mpsi while having an elastic range or strain of at least 0.7% or at least 0.8% or at least 0.9% or at least 1% or at least 1.1% or at least 1.2%. In many embodiments the annealed Ti-15Mo material has an elastic range upper value or strain value in a range of 1 to 2%. in a range of 1.2 to 2.0%. The annealed Ti-15Mo material has a mean average grain size value of less than 30 micrometers or in a range from 1 to 30 micrometers or in a range from 5 to 20 micrometers.

These physical properties of the resiliently deflectable elements provides for unique features when utilized in a lead receptacle for a medical device. For example, a lead connector or receptacle having these contact elements has a reduced lead insertion force into the lead receptacle thus, a lead can be easily inserted the lead receptacle. At the same time the resiliently deflectable elements securely contact the lead body and elastically move relative to inserting and removing the lead from the lead receptacle. In other words, the resiliently deflectable elements do not plastically or permanently deform upon insertion of the lead into the lead receptacle.

Referring to FIG. 7 is a flow diagram of an illustrative method 700 of forming a medical device contact element 300. The method includes annealing a rod of titanium alloy at block 710, then forming a contact ring element from the annealed rod at block 720, and then assembling the contact ring element into a medical device at block 730. The method can further include a cold draw or cold roll prior to annealing. The titanium alloy can be the Ti-15Mo material described above and the annealing processing parameters are described above to achieve the physical properties described above.

Thus, embodiments of the TITANIUM ALLOY CONTACT RING ELEMENT HAVING LOW MODULUS AND LARGE ELASTIC ELONGATION are disclosed. All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A method comprising:
    annealing an elongated rod of Ti-15Mo alloy material to form a solid, annealed rod having an outer diameter between 2 mm and 10 mm and comprising alpha-phase titanium in an amount up to 3 wt %, a Young's Modulus of less than 13.5 Mpsi, and a mean average grain size value of up to 30 micrometers; and
    forming a contact ring element from the annealed rod configured to receive a lead.

2. The method according to claim 1, wherein the contact ring element comprises a tubular body defining a cavity configured to receive the lead and the contact ring element further comprises one or more resiliently deflectable elements extending from the tubular body into the cavity.

3. The method according to claim 2, wherein the contact ring element comprises a plurality of the one or more resiliently deflectable elements extending from the tubular body into the cavity.

4. The method according to claim 2, wherein the one or more resiliently deflectable elements each have a thickness between 0.025 mm and 0.25 mm.

5. The method according to claim 2, wherein a thickness of the contact ring element varies along a length of the one or more resiliently deflectable elements.

6. The method according to claim 1, wherein the contact ring element is monolithic.

7. The method according to claim 1, wherein the annealed rod comprises the alpha-phase titanium in an amount up to 2 wt %.

8. The method according to claim 1, wherein the annealed rod comprises a mean average grain size value of up to 20 micrometers.

9. The method according to claim 1, further comprising water quenching the annealed rod.

10. The method according to claim 9, wherein the annealing step comprises annealing at a temperature in a range from 725 to 775 degrees centigrade for 5 to 30 minutes and then water quenching.

11. The method according to claim 9, wherein the annealing step comprises annealing at a temperature in a range from 740 to 750 degrees centigrade for 10 to 20 minutes and then water quenching.

12. The method according to claim 9, wherein the annealing step comprises annealing at a temperature in a range from 740 to 750 degrees centigrade for 15 minutes and then water quenching.

13. The method according to claim 1, further comprising:
    dividing the annealed rod into a plurality of subunits; and
    removing a portion of at least selected subunits to form a cavity of the contact ring element.

14. The method according to claim 13, wherein the removing step forms one or more resiliently deflectable elements extending from a tubular body into the cavity.

15. The method according to claim 14, further comprising assembling the contact ring element into a medical device.

16. The method according to claim 15, wherein the assembling step comprises axially aligning a plurality of contact ring elements to form a lead receptacle for receiving the lead, wherein the lead elastically deflects the one or more resiliently deflectable elements.

17. The method according to claim 13, wherein the removing step comprises electrical discharge machining.

18. The method according to claim 1, wherein the contact ring element has a thickness up to 2.5 mm.

19. The method according to claim 1, wherein the contact ring element has an outer diameter between 1.2 mm and 5 mm.

* * * * *